(12) United States Patent
Yabushita et al.

(10) Patent No.: US 8,024,975 B2
(45) Date of Patent: Sep. 27, 2011

(54) ULTRASONIC TESTING METHOD AND ULTRASONIC TESTING DEVICE USING THIS

(75) Inventors: Hideki Yabushita, Chiba (JP); Tatsuyuki Nagai, Osaka (JP); Shigeyuki Matsubara, Osaka (JP); Norio Nemoto, Ibaraki (JP); Hiroshi Miyamoto, Chiba (JP)

(73) Assignees: Independent Administrative Institution Japan Aerospace Exploration Agency, Tokyo (JP); Non-Destructive Inspection Company Limited, Osaka (JP)

( * ) Notice: Subject to any disclaimer, the term of this patent is extended or adjusted under 35 U.S.C. 154(b) by 797 days.

(21) Appl. No.: 11/988,306

(22) PCT Filed: Jun. 30, 2006

(86) PCT No.: PCT/JP2006/313121
§ 371 (c)(1),
(2), (4) Date: May 22, 2008

(87) PCT Pub. No.: WO2007/004574
PCT Pub. Date: Jan. 11, 2007

(65) Prior Publication Data
US 2008/0302188 A1 Dec. 11, 2008

(30) Foreign Application Priority Data
Jul. 4, 2005 (JP) ................................. 2005-195600

(51) Int. Cl.
*G01N 29/04* (2006.01)
*G01N 29/00* (2006.01)

(52) U.S. Cl. .............................. 73/628; 73/632; 73/661
(58) Field of Classification Search ................... 73/579, 73/618–621, 624–629, 632–634, 649, 661
See application file for complete search history.

(56) References Cited

U.S. PATENT DOCUMENTS
4,100,809 A * 7/1978 Bobrov et al. .................. 73/638
(Continued)

FOREIGN PATENT DOCUMENTS
JP 42-14635 Y1 8/1967
(Continued)

OTHER PUBLICATIONS
Notice of Allowance mailed on Feb. 19, 2008 (Japan).
(Continued)

*Primary Examiner* — Helen C. Kwok
(74) *Attorney, Agent, or Firm* — Rader, Fishman & Grauer PLLC

(57) ABSTRACT

An ultrasonic wave is sent from a transmission element to a test element to produce a plate wave in the test element, and the plate wave propagating through the test element is received by a reception element to thereby test the test element on the propagation route of the plate wave. The other probe that is the other reception element or transmission element is disposed between the transmission element and the reception element. A probe holding mechanism that has support legs contacting the surface of the test element and keeps constant an angle of the other probe with respect to the surface of the test element is allowed to support the other probe. And, the other probe is allowed to cross over in non-contact the propagation route of the plate wave extending from the transmission element to the reception element by means of support legs.

11 Claims, 7 Drawing Sheets

U.S. PATENT DOCUMENTS

| | | | |
|---|---|---|---|
| 6,092,421 A * | 7/2000 | Bar-Cohen et al. | 73/624 |
| 7,721,606 B2 * | 5/2010 | Shirai et al. | 73/627 |
| 2009/0165561 A1 * | 7/2009 | Yabushita et al. | 73/597 |

FOREIGN PATENT DOCUMENTS

| | | |
|---|---|---|
| JP | 62-222161 A | 9/1987 |
| JP | 63-175762 A | 7/1988 |
| JP | 63-241349 A | 10/1988 |
| JP | 02-154147 A | 6/1990 |
| JP | 06-05624 Y2 | 2/1994 |
| JP | 09-281089 A | 10/1997 |
| JP | 09-304355 A | 11/1997 |
| JP | 10-038862 A | 2/1998 |
| JP | 2000-028589 A | 1/2000 |
| JP | 2002-022431 A | 1/2002 |
| JP | 2003-254947 A | 9/2003 |
| JP | 2004-212308 A | 7/2004 |
| JP | 2005-055197 A | 3/2005 |

OTHER PUBLICATIONS

Office Action mailed on Dec. 5, 2007 (Japan).

O. Fukada, "Air Coupling Type Ultrasonic Flaw Detecting Device AIR SCAN", *Inspection Engineering*, vol. 6, No. 12, pp. 58-61 (Japan).

International Preliminary Report (International Application No. PCT/JP2006/313121) mailed on Apr. 24, 2008.

* cited by examiner

ULTRASONIC TESTING METHOD AND ULTRASONIC TESTING DEVICE USING THIS

FIELD OF THE INVENTION

The present invention relates to an ultrasonic testing method for transmitting an ultrasonic wave from a transmitter to generate a plate wave in a test piece and receiving at a receiver the plate wave passed through the test piece to inspect the test piece along the propagation path of the plate wave, and an ultrasonic testing device using the ultrasonic testing method.

BACKGROUND OF THE INVENTION

One of such ultrasonic testing devices as described above is known where a sensor head is provided comprising two or more of the transmitters and the receivers disposed at both ends of the center point and particularly held at a uniform angle (the incident angle) to the test piece for scanning the surface of the test piece with no direct contact (See Patent Document 1). It is essential for maintaining the incident angle to a uniform degree to match different modes of the relationship between the incident angle of the ultrasonic wave and the product of ultrasonic frequency and test piece thickness with their respective characteristic curves.
Patent Document 1: Japanese Patent Laid-open Publication No. 2005-055197.

However, if the surface of the test piece is undulated or waved, the incident angle between the transmitter or receiver and the surface of the test piece may hardly be maintained at a uniform degree during the scanning action with no direct contact of the sensor head, thus interrupting the inspecting action with the plate wave.

Alternatively, another testing method is known for inspecting a test piece with the transmitter and receiver placed directly on the test piece. However, the another method also fails to propagate the plate wave up to the receiver after the point on the propagation path of the plate wave where the transmitter or receiver is placed directly on the test piece, hence permitting no use of two or more of the receivers.

More specifically, the conventional methods allows the transmitter or receiver to be disposed across the propagation path of the plate wave which extends through the target region of a test piece to be inspected when the inspection depend fundamentally on the leak wave or the reflection of the ultrasonic wave. As a result, the degree of freedom of the testing action will be limited due to a limited target area of the test piece. Also, with no use of two or more transmitters or receivers, the testing action may hardly be improved in the efficiency.

SUMMARY OF THE INVENTION

It is hence a first object of the present invention, in view of the foregoing aspects, to provide an ultrasonic testing method for, while increasing the degree of freedom for allocating a transmitter and a receiver, ensuring the action of inspection at higher degree of freedom with less limitation of the target area of a test piece to be inspected and to an ultrasonic testing device using this ultrasonic testing method.

It is a second object of the present invention to provide an ultrasonic testing method for allocating a set of receivers thus to improve the efficiency of the action of inspection and to an ultrasonic testing device using this ultrasonic testing method.

For achievement of the object of the present invention, an ultrasonic testing method for transmitting an ultrasonic wave from a transmitter to generate a plate wave in a test piece and receiving at a receiver the plate wave passed through the test piece to inspect the test piece along the propagation path of the plate wave is provided comprising the steps of: providing a probe, which acts as either another transmitter or another receiver, between the transmitter and the receiver which are arranged for transmitting or receiving the ultrasonic wave across a gaseous substance; mounting the transmitter, the receiver, and the probe on probe holding mechanisms respectively which have support legs thereof placed directly on the surface of the test piece, which is selected from aerospace devices, composite materials, and lengthened materials having curves, bends, or branches, and are arranged movable in relation to the test piece so that the transmitter or the receiver can remain held at a desired angle to the surface of the test piece; holding the support legs in direct contact with the surface of the test piece at a location off the propagation path of the plate wave extending from the transmitter to the receiver so that the probe is suspended by the support legs to bridge, with no direct contact, over the propagation path while the probe holding mechanisms are arranged to move the transmitter, the receiver, and the probe simultaneously in relation to the test piece; and passing the plate wave beneath the probe while directing the probe to transmit the ultrasonic wave or receive the plate wave.

As another feature of the present invention, an ultrasonic testing method for transmitting an ultrasonic wave from a transmitter to generate a plate wave in a test piece and receiving at a receiver the plate wave passed through the test piece to inspect the test piece along the propagation path of the plate wave is provided comprising the steps of: emitting the plate wave at the forward route from the transmitter and receiving its reflection reflected by a target region of the test piece with the receiver, the transmitter and the receiver both arranged for transmitting or receiving the ultrasonic wave across a gaseous substance; mounting the transmitter and the receiver on probe holding mechanisms respectively which have support legs thereof placed directly on the surface of the test piece, which is selected from aerospace devices, composite materials, and lengthened materials having curves, bends, or branches, and are arranged movable in relation to the test piece so that the transmitter or the receiver can remain held at a desired angle to the surface of the test piece; holding the support legs in direct contact with the surface of the test piece at a location off the propagation path of both the forward route of the plate wave and the reflection of the plate wave so that the transmitter and the receiver are suspended by the support legs to bridge, with no direct contact, over the propagation path of both the forward route of the plate wave and the reflection of the plate wave while the probe holding mechanisms are arranged for moving the transmitter and the receiver simultaneously in relation to the test piece; and passing the plate wave emitted from the transmitter, reflected by the target region of the test piece, and propagated towards the receiver beneath the transmitter or the receiver located on the way of the propagation path while transmitting the ultrasonic wave from the transmitter or receiving the reflection of the plate wave with the receiver.

Each of the foregoing methods may be modified in which the probe is a focusing type probe. Alternatively, the test piece may be divided into target regions to be inspected to which the receivers are allocated respectively.

The method may further be modified in which the transmitter and the receiver are moved in relation to the test piece along a direction which extends at a right angle to the propagation path of the plate wave. Alternatively, the transmitter and the receiver may be moved in relation to the test piece along a direction aligned with the propagation path of the plate wave.

An ultrasonic testing device having a transmitter for emitting an ultrasonic wave towards a test piece to generate a plate wave in the test piece and a receiver for receiving the plate wave passed through the test piece, whereby the test piece can be inspected along the propagation path of the plate wave by the receiver receiving the plate wave, according to the present invention is provided comprising probe holding mechanisms for holding the transmitter and the receiver respectively which are arranged for transmitting or receiving the ultrasonic wave across a gaseous substance, each the probe holding mechanism having support legs thereof placed directly on the surface of the test piece, which is selected from aerospace devices, composite materials, and lengthened materials having curves, bends, or branches, and arranged movable in relation to the test piece so that the transmitter or the receiver can remain held at a desired angle to the surface of the test piece; a supporting frame provided to which the probes holding mechanisms are mounted so that the transmitter and the receiver can move simultaneously in relation to the test piece; and pressing members provided for urging the support legs of the probe holding mechanisms by pressure directly against the surface of the test piece downwardly of the supporting frame at a location off the propagation path of the plate wave so that the transmitter and the receiver are suspended by the support legs to bridge, with no direct contact, over the propagation path of the plate wave.

Another ultrasonic testing device for use with any of the foregoing methods according to the present invention is provided as characterized in that the transmitter and the receiver are held by their respective probe holding mechanisms of which the support legs are spaced from each other to clear at least the propagation path of the plate wave, and each of the probe holding mechanisms is mounted to a supporting frame while remains urged by a pressing member against the supporting frame so that its support legs are placed directly on the surface of the test piece and is further accompanied with a rocking mechanism provided between the probe holding mechanism and the supporting frame for rocking its transmitter or receiver on the axis which extends at a right angle to the propagation path of the plate wave in relation to the supporting frame.

A further ultrasonic testing device for use with any of the foregoing methods according to the present invention is provided as characterized in that the supporting legs of the probe holding mechanism are equipped with wheels for running thus to move the transmitter and receiver in relation to the test piece.

A still further ultrasonic testing device for transmitting an ultrasonic wave from a transmitter to generate a plate wave in a test piece and receiving at a receiver the plate wave passed through the test piece to inspect the test piece along the propagation path of the plate wave is provided as characterized in that the transmitter and the receiver are held by their respective probe holding mechanisms, each probe holding mechanism having support legs thereof placed directly on the surface of the test piece and arranged for holding the transmitter or receiver at a uniform angle to the surface of the test piece, the support legs of each probe holding mechanism are spaced from each other to clear at least the propagation path of the plate wave, and each of the probe holding mechanisms is mounted to a supporting frame while remains urged by a pressing member against the supporting frame so that its support legs are placed directly on the surface of the test piece and is further accompanied with a rocking mechanism provided between the probe holding mechanism and the supporting frame for rocking its transmitter or receiver on the axis which extends at a right angle to at least the propagation path of the plate wave in relation to the supporting frame.

The ultrasonic testing method and the ultrasonic testing device using the method according to the present invention allows each probe to be held by its corresponding probe holding mechanism and the transmitter to be suspended by the support legs of the probe holding mechanism to bridge, with no direct contact, over the propagation path of the plate wave, whereby the plate wave can hardly be interrupted while the allocation of the transmitter and the receiver is improved in the degree of freedom with the target area to be inspected of the test piece less limited thus ensuring a higher effectiveness of the testing action.

Also, since an extra probe which may be a transmitter or a receiver is disposed between the transmitter and the receiver, either the transmission of plural kinds of the ultrasonic wave or the reception of the ultrasonic wave can be implemented at two or more locations, thus increasing the efficiency of the testing action.

Other objects, arrangements, and advantages will be apparent from the following description of some embodiments of the present invention.

DESCRIPTION OF NUMERALS AND SYMBOLS

Figure 1A:
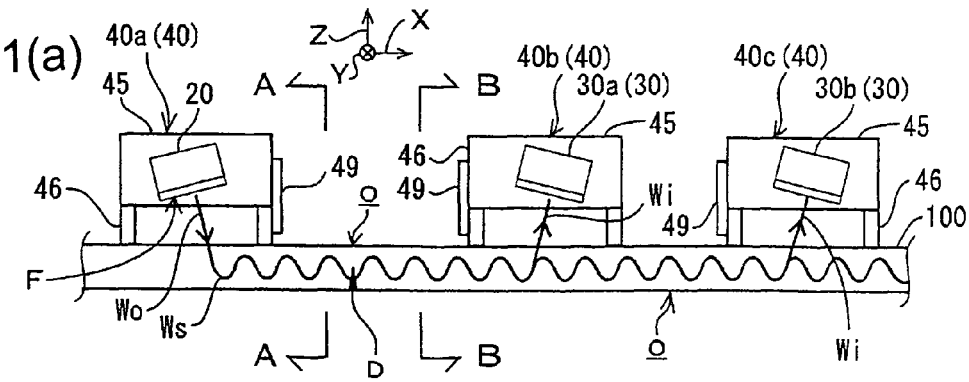
FIG. 1 illustrates an example of the testing method according to the present invention, showing a side view at FIG. 1A, a cross sectional view at FIG. 1B taken along the line A-A of FIG. 1A, a cross sectional view at FIG. 1C taken along the line B-B of FIG. 1A, a side view of another example of the testing method at FIG. 1D, and a side view of a further example of the testing method at FIG. 1E.

1: Ultrasonic testing device, 2: PC, 3: Plate wave transducer, 4. Preamplifier, 5: Filter, 6: A/D converter, 7: Driver, 8: Scanner, 10: Scanning head, 11: Supporting frame, 20: Transmitter, 30: Receiver, (30a: First receiver, 30b: Second receiver, 30c: Third receiver, 30d: Fourth receiver), 40: Probe holding mechanism, 41: Shaft, 42: Direct-action bearing, 43: Pressing member (spring), 44: Rocking mechanism, 44a: Convex surface, 44b: Concave surface, 45: Housing, 45a: Window, 46: Support legs, 46a: Legs, 46b: Wheels, 47: Tightening clamp, 47a: Probe supporting shaft, 49: Shielding member, 100: Test piece, 100a: First flange, 100b: Second flange, 100c: First branching point, 100d: Web, 100e: Second branching point, 100f: Third flange, 100g: Fourth flange, D: Defect, O: Target region to be inspected, F: Probe surface, Wo: Transmitting wave, Ws: (Forward) plate wave, Wi: Leak wave, Wr: Reflected wave.

BEST MODES FOR EMBODYING THE INVENTION

A first embodiment of the present invention will be described referring to the accompanying drawings FIGS. 1 to 7.

As shown in FIG. 5 and FIGS. 1A to 1C, an ultrasonic testing device 1 is designed for transmitting an ultrasonic wave from the transmitter 20 in a scan head 10 with the use of a plate wave transducer 3 which is controlled by a personal computer 2 (referred to simply a PC hereinafter). While the ultrasonic wave is propagated between the support legs 46 of a probe holding mechanism 40a which contains a transmitter 20 and the support legs 46 of another probe holding mechanism 40b which contains a receiver 30, it generates a plate wave Ws in a test piece 100. This allows a leak wave Wi to be received and transferred via a pre-amplifier 4, a filters 5, and an A/D converter 6 to the PC 2 where it is subjected to arithmetic operations. The PC 2 also turns a scanner 8 on via a driver 7 for starting the scanning action of the scan head 10 to detect any flaw in the test piece 100. A sensor 10x is provided between the scan head 10 and the test piece 100 for acquiring a data about the scanning position of the scan head 10.

Figure 2:
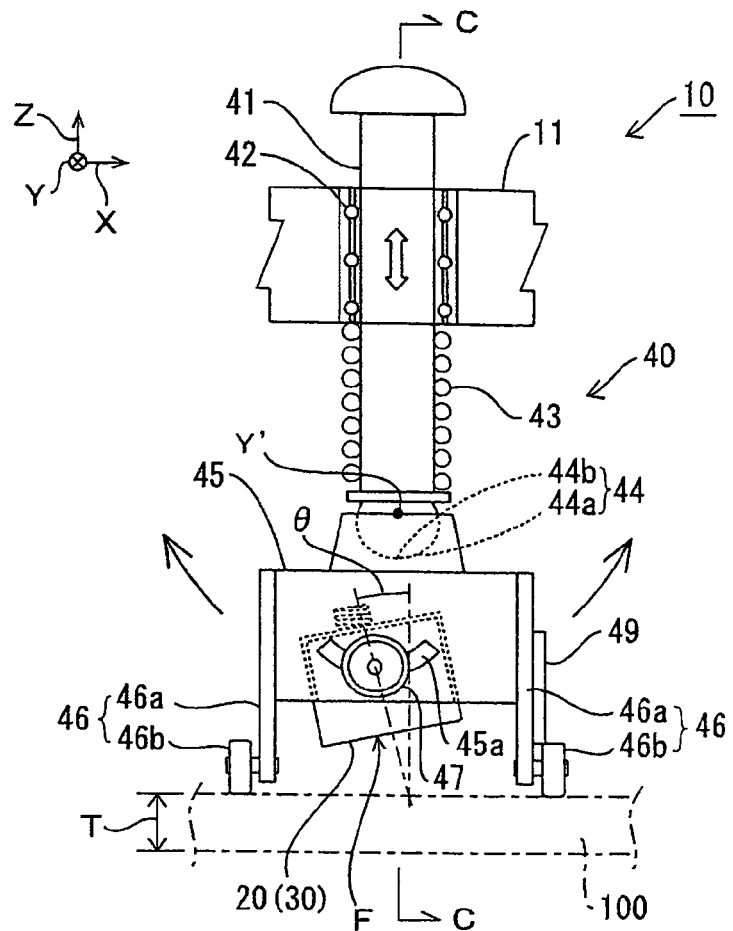
FIG. 2 is a partially cross sectional side view showing the first embodiment of the present invention.
Figure 3:
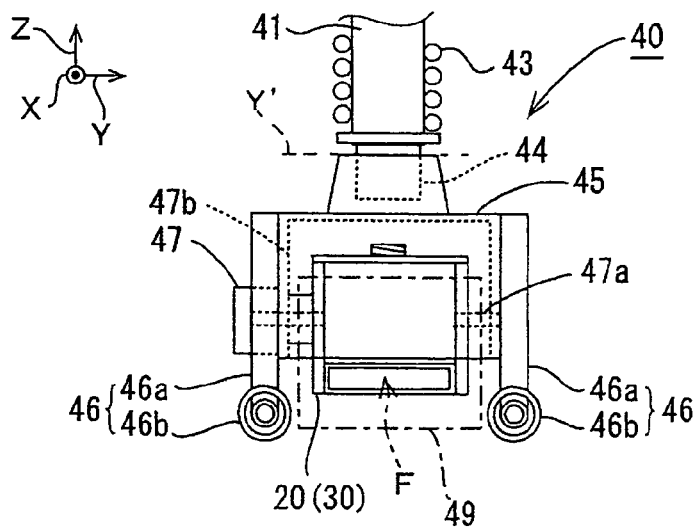
FIG. 3 is a partially cross sectional side view taken along the line C-C of FIG. 2.

The scan head 10 comprises, as best shown in FIGS. 2 and 3, a supporting frame 11 supporting a set of the probe holding mechanisms 40, the transmitter 20, the receiver 30, and the probe holding mechanisms 40. The probe holding mechanism 40 comprises a direct-acting bearing 42, a pressing member 43, a rocking mechanism 44, a housing 45, the support legs 46, a tightening clamp 47, and a shielding member 49.

The probe holding mechanism 40 is joined by the direct-acting bearing 42 to the supporting frame 11 so that its shaft 41 can move vertically of the supporting frame 11. The shaft 41 remains urged by the pressing member 43, such as a compression coil spring, to press against the test piece 100 downwardly of the supporting frame 11. The rocking mechanism 44 consists mainly of a convex, arcuate side 44a provided on one end of the shaft 41 and a concave, arcuate side 44b provided on the housing 45, whereby the housing 45 can be rocked about the Y' axis which extends along at least the Y axis. As the result, the support legs 46 come equally into direct contact with the upper surface of the test piece 100, thus holding the transmitter 20 and the receiver 30 at constant angles to the upper surface of the test piece 100. The rocking mechanism 44 may be arranged for rocking movement about any axis other than the Y' axis.

The support leg 46 consists mainly of a leg portion 46a located at each corner of the four-sided bottom of the housing 45 and a wheel 46b mounted to the leg portion 46a for running along the Y so as to roll directly on the upper surface of the test piece 100 with smoothness. The tightening clamp 47 tightly clamps probe supporting shaft 47a which extends across a window 45a provided in the housing 45. This allows each of the transmitter 20 and the receiver 30 to be held at a desired degree of the incident (receivable) angle θ to the test piece 100.

Figure 6:
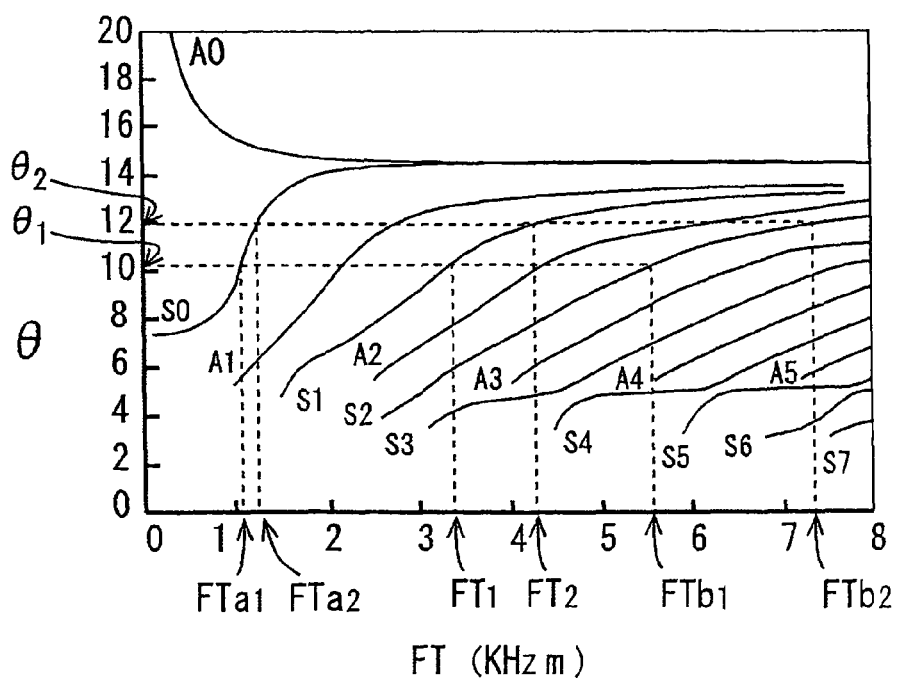
FIG. 6 is a graphic diagram showing the relationship at different modes (denoted by A0 to A5, S0 to S7) of the plate wave between the product of the frequency of an ultrasonic wave and the thickness of a test piece.

FIG. 6 is a graphic diagram showing the relationship between the product FT of the frequency F of the ultrasonic wave and the thickness T of the test piece 100 and the incident angle θ at different modes (denoted by A0 to A5 and S0 to S7) of the plate wave Ws when the test piece 100 is made of a steel plate. While the relationship at each mode is satisfied, the plate wave Ws at the mode is generated in the test piece 100 and can thus be applied to inspection of a target region O of the test piece 100 as shown in FIG. 1.

Figure 7A:
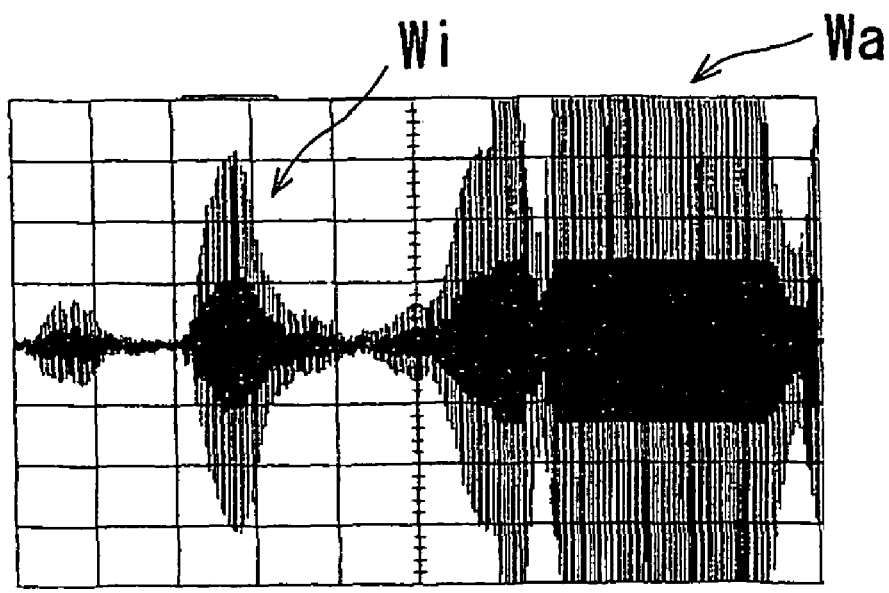
FIG. 7 is a graphic diagram of waveforms of the lead wave received, showing the absence of a defect at FIG. 7A and the presence of a defect at FIG. 7B.
Figure 7B:
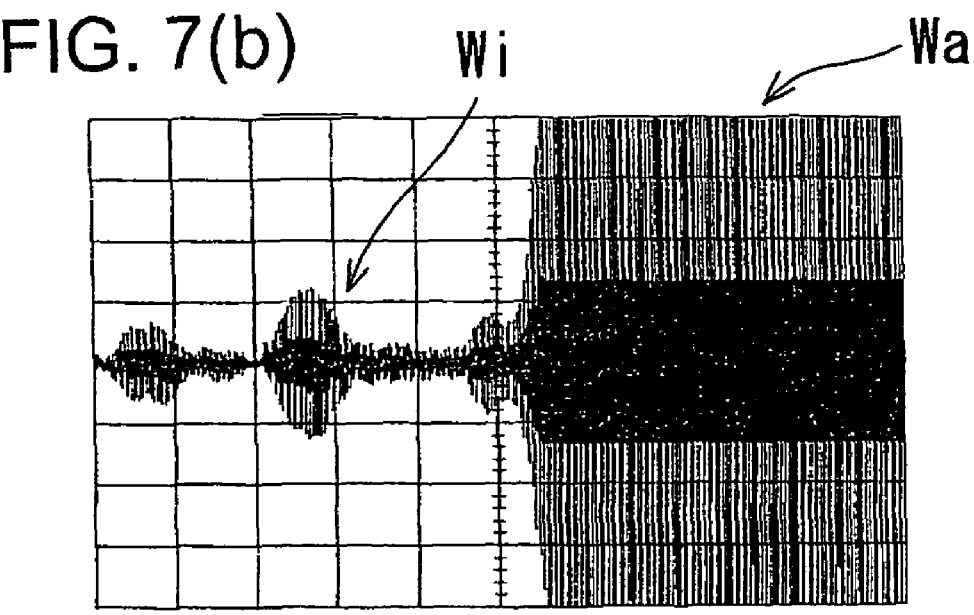

FIG. 7 illustrates waveforms of the leak wave Wi produced at the target region and received by the receiver 30. While a portion of the ultrasonic wave passed through the target region of the test piece 100 is first measured, the remaining Wa of the ultrasonic wave passed directly through the air is received with a delay of time. When the target region O has no defect, its resultant waveform is normally as large as shown in FIG. 7A. If the target region O has a defect D such as a peel, its resultant waveform as the lead wave Wi measured first is as small as shown in FIG. 7B. The shielding member 49 mounted to one side of the housing 45 has a function for delaying the propagation and thus reception through the air of the ultrasonic wave. The shielding member 49 may be made of paper or synthetic resin material.

Some variations of the action of testing the test piece 100 will be described referring to FIG. 1. In the variations of the testing action shown in FIGS. 1A to 1C, the ultrasonic wave Wo is emitted from the transmitter 20 to the test piece 100 where it generates a forward plate wave Ws. The resultant leak wave Wi passed through the test piece 100 is then received by the receiver 30.

Each of the transmitter 20, the first receiver 30a, and the second receiver 30b used in those variations of the testing action is installed in the housing 45 as supported by the four support legs 46 mounted to the outer edges of the housing 45 for sitting directly on the upper surface of the test piece 100. As shown in FIGS. 1B and 1C, the supporting legs 46 allows the transmitter 20 and the first receiver 30a to be distanced with no direct contact from the test piece 100 while bridging over the forward plate wave Ws propagated through the test piece 100.

Figure 1B:
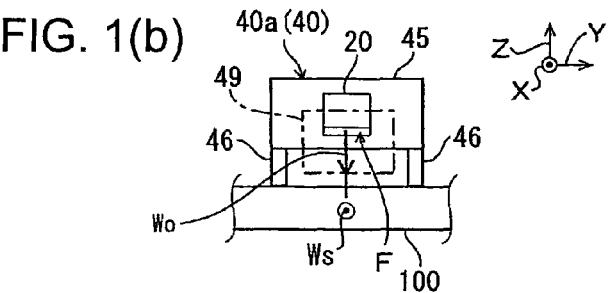
Figure 1C:
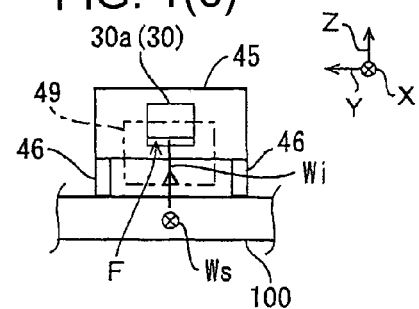

In the variation of the action shown in FIG. 1A, the first receiver 30a is located between the transmitter 20 and the second receiver 30b. Accordingly, two of the target regions O of the test piece 100 are designated between the transmitter 20 and the first receiver 30a and between the first receiver 30a and the second receiver 30b. Since the propagation path of the forward plate wave Ws is not disturbed by the support legs 46, the first receiver 30a can be located between. This allows the leak wave Wi to be received at two different positions, hence increasing the area to be inspected with positional accuracy.

Figure 1D:
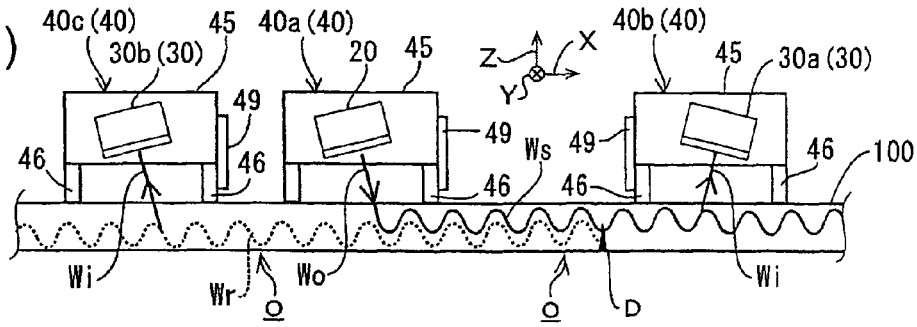

Alternatively, the transmitter 20 may be disposed between the first receiver 30*a* and the second receiver 30*b* as shown in FIG. 1D. This allows the leak wave Wi to be received as a transmitted wave by the first receiver 30*a* and as a reflected wave Wr by the second receiver 30*b*.

Figure 1E:
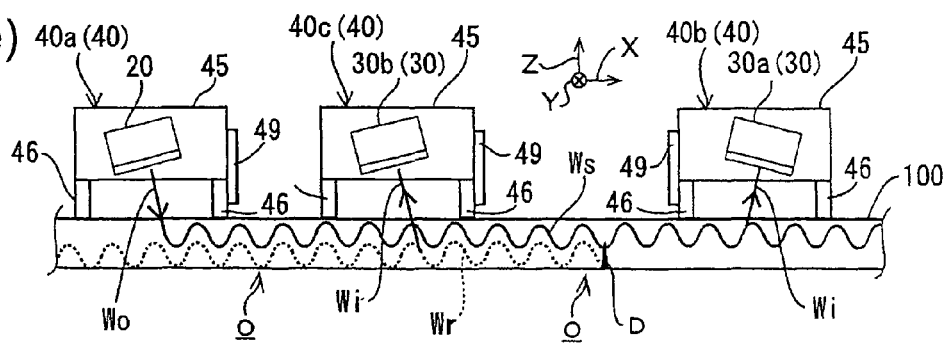

Moreover, the second receiver 30*b* may be disposed between the transmitter 20 and the first receiver 30*a*, as shown in FIG. 1E, for receiving as the leak wave Wi the reflection Wr of the ultrasonic wave produced by a defect D. This is advantageous because the leak wave Wi is received regardless of the orientation of the second receiver 30*b* as is equally applicable to the arrangement shown in FIG. 1A.

Figure 4:
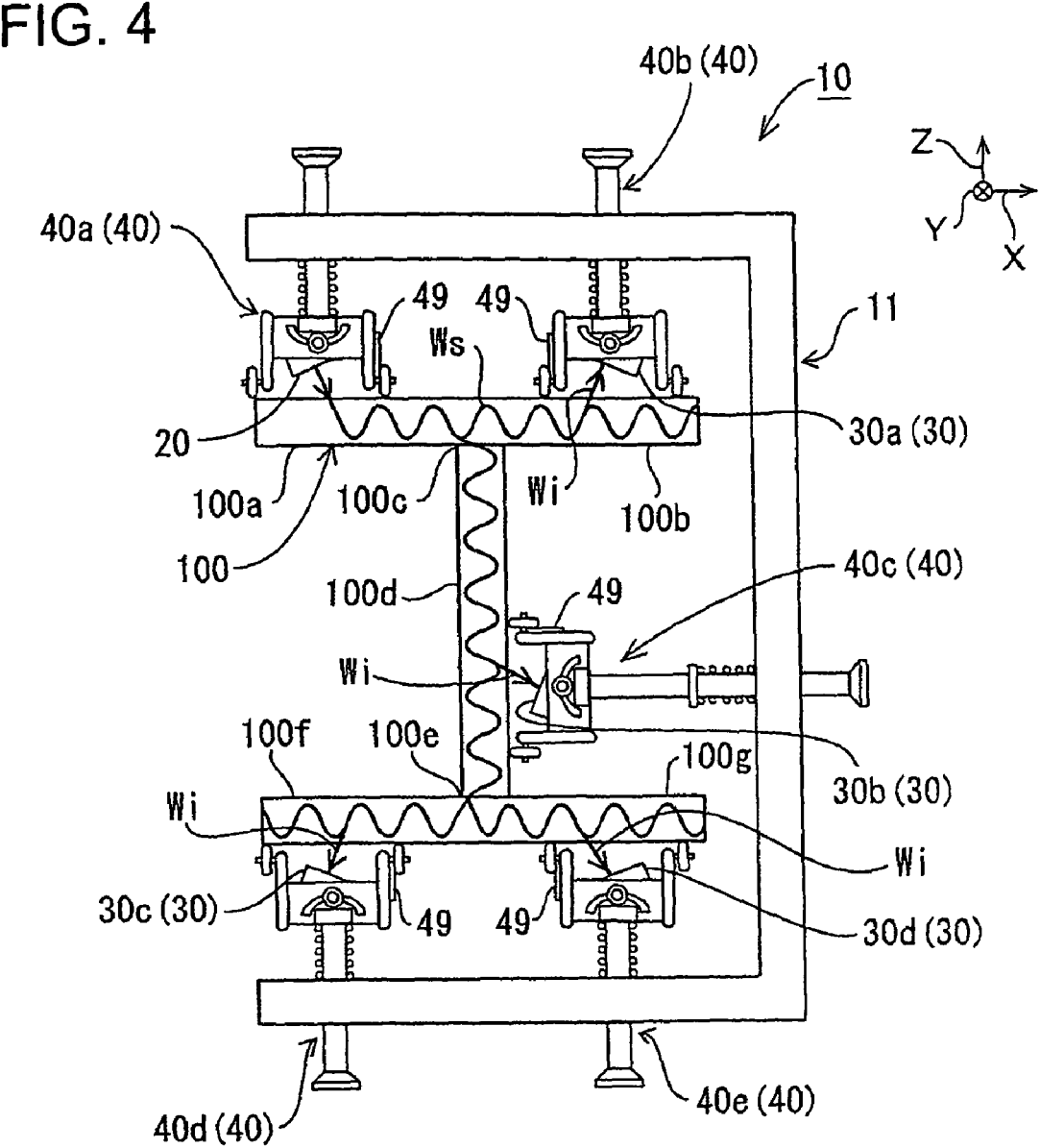
FIG. 4 is a side view showing a modification of the first embodiment of the present invention.
Figure 5:
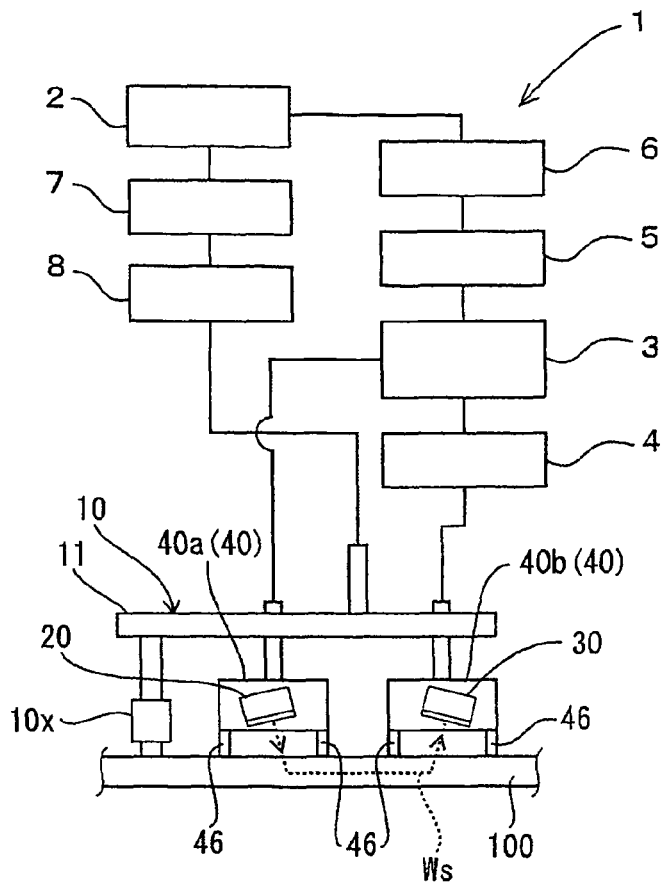
FIG. 5 is a schematic view of a testing device according to the present invention.

FIG. 4 illustrates a feasible example for conducting the variations of the testing action shown in FIG. 1. As apparent, the test piece 100 has an I-shape which comprises a first flange 100*a*, a second flange 100*b*, a web 100*d*, a third flange 100*f*, and a fourth flange 100*g* as extending in two opposite directions frontwardly and rearwardly of the paper sheet (along the Y direction). The transmitter 20 and the four receivers 30*a* to 30*d* are held by their respective probe holding mechanisms 40*a* to 40*e* and joined to the supporting frame 11 of a channel form. The sensor head 10 carrying the probe holding mechanisms 40*a* to 40*e* is movable for running with the wheels 46*b* of the mechanisms 40*a* to 40*e* along the Y direction.

In action, the forward plate wave Ws emitted from the transmitter 20 and propagated through the first flange 100*a* separates at a first branching point 100*c* into two along the second flange 100*b* and the web 100*d*. The plate wave Ws is further separated at a second branching point 100*e* into two along the third flange 100*f* and the fourth flange 100*g* before received as the leak waves Wi by the corresponding receivers 30. Accordingly, since its ultrasonic wave is received simultaneously by a group of positions, the testing action can be improved in the operational efficiency.

Other embodiments of the present invention will be described. Like components are denoted by like numerals as those of the previous embodiments and will be explained in no more detail.

Figure 8:
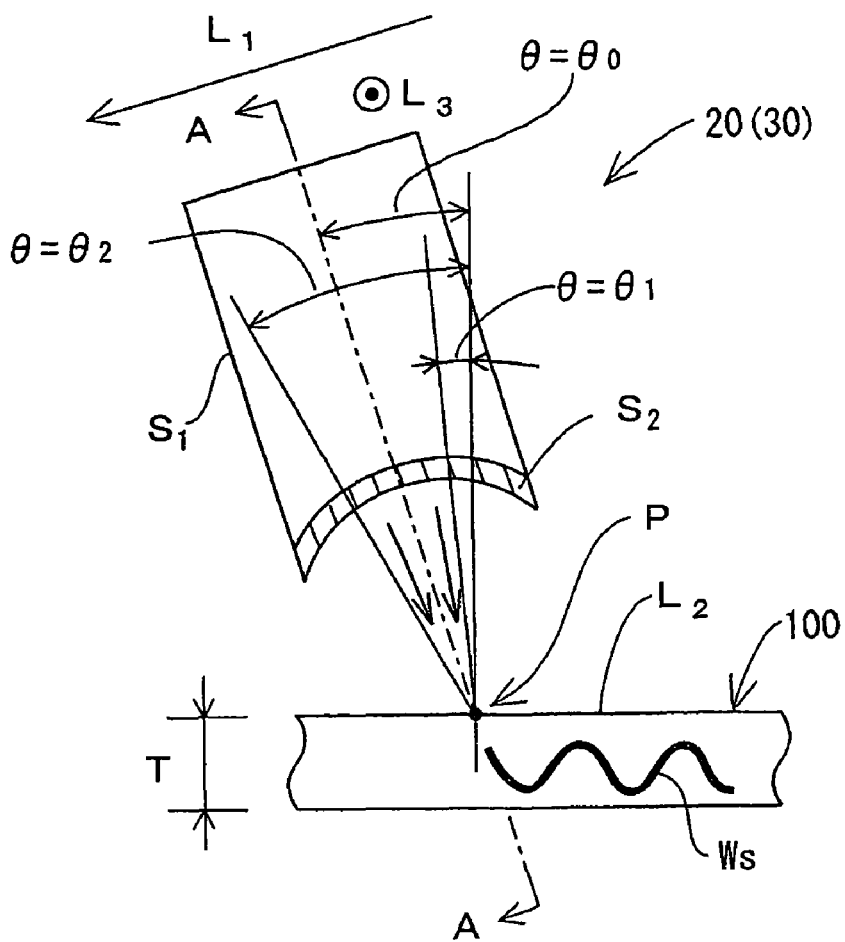
FIG. 8 is a partially cross sectional view of a testing device showing the second embodiment of the present invention.

FIG. 8 illustrates a second embodiment of the present invention in which the transmitter 20 and the receiver 30 are implemented by focusing type probes S2 of which the oscillator is curved. This allows the incident angle θ to be set to a desired degree ranging widely from θ1 to θ2. Accordingly, the testing action can respond to small undulations of the surface of the test piece 100 which may interrupt the action of the probe holding mechanisms 40 and overcome any fitting fault between the support legs 46 and the test piece 100.

Figure 9:
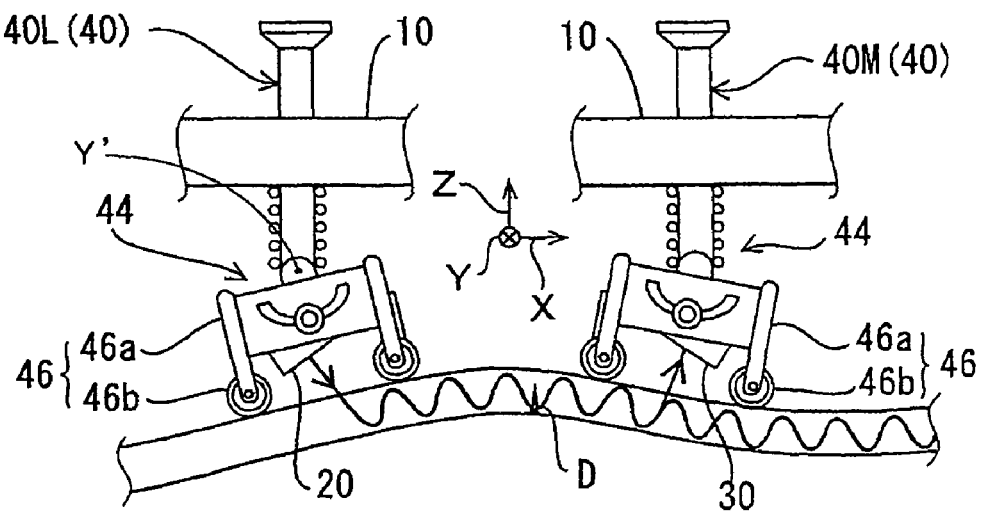
FIG. 9 is a partially cross sectional view of a testing device showing the third embodiment of the present invention.

FIG. 9 illustrates a third embodiment of the present invention in which the wheels 46*b* of the support legs 46 are arranged at a right angle, ninety degrees, to those of the first embodiment. More specifically, the probe holding mechanisms 40 are classified into probe holding mechanisms 40L equipped with the wheels 46*b* and the transmitters 30 and probe holding mechanisms 40M equipped with the wheels 46*b* and the receivers 40. Accordingly, since its scanning action along the X direction is enabled, the testing action can respond to undulations of the surface or XY plane of the test piece 100 in combination with the function of the rocking mechanisms 44.

Figure 10A:
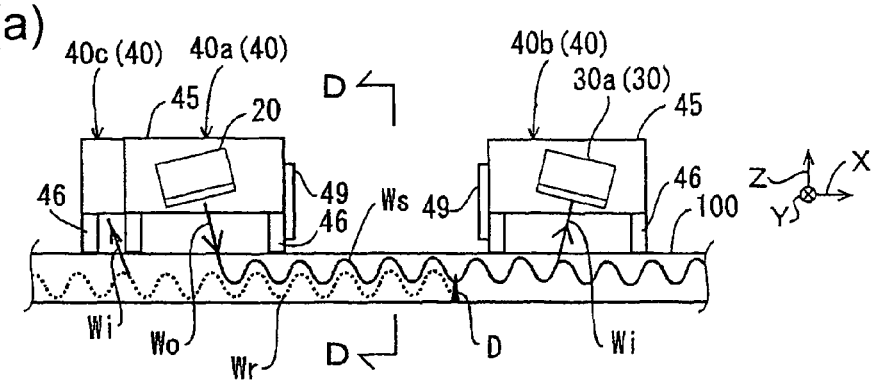
FIG. 10 illustrates a fourth embodiment of the present invention (which is not disclosed in claims but explained as a reference) in which a pair of a probe holding mechanism 40c carrying the second receiver 30b and a probe holding mechanism 40a carrying the transmitter 20 are aligned along the Y direction. Also, a probe holding mechanism 40b carrying the first receiver 30a is provided for receiving a portion of the forward plate wave Ws transmitted across a defect D while the probe holding mechanism 40c receives the reflection Wr of the plate wave.
Figure 10B:
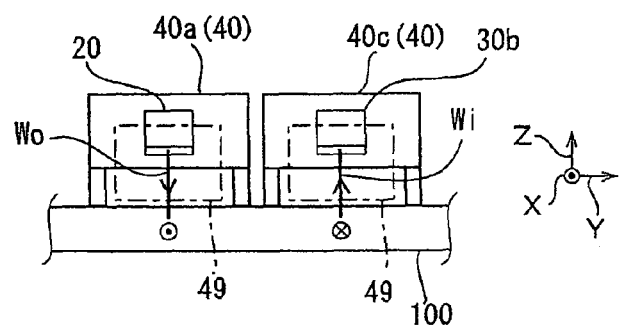
Figure 10C:
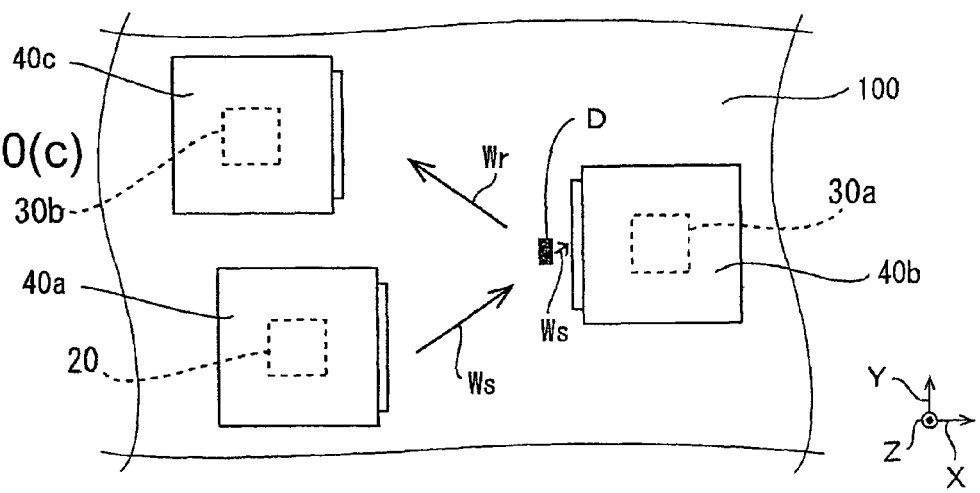

FIG. 10 illustrates a fourth embodiment of the present invention (which is not disclosed in claims but explained as a reference) in which a pair of a probe holding mechanism 40*c* carrying the second receiver 30*b* and a probe holding mechanism 40*a* carrying the transmitter 20 are aligned along the Y direction. Also, a probe holding mechanism 40*b* carrying the first receiver 30*a* is provided for receiving a portion of the forward plate wave Ws transmitted across a defect D while the probe holding mechanism 40*c* receives the reflection Wr of the plate wave.

Figure 11:
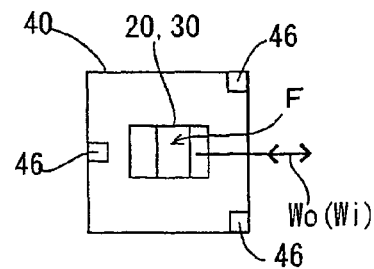
FIG. 11 illustrates a fifth embodiment of the present invention which is differed by the fact that the probe holding mechanism 40 is supported by three of the support legs 46. In this embodiment, the transmission and reception of the transmission wave Wo and the leak wave Wi is carried out between the support legs 46 which thus guarantee no interruption of the propagation of the plate wave Ws, ensuring the smoothness of the testing action. This embodiment is advantageous particularly when the probes 20, 30 are positioned at edges of the target region O of the test piece 100. In case that the probe holding mechanism 40 is placed to bridge the target region O to be inspected, the other embodiments are favorable.

FIG. 11 illustrates a fifth embodiment of the present invention which is differed by the fact that the probe holding mechanism 40 is supported by three of the support legs 46. In this embodiment, the transmission and reception of the transmission wave Wo and the leak wave Wi is carried out between the support legs 46 which thus guarantee no interruption of the propagation of the plate wave Ws, ensuring the smoothness of the testing action. This embodiment is advantageous particularly when the probes 20, 30 are positioned at edges of the target region O of the test piece 100. In case that the probe holding mechanism 40 is placed to bridge the target region O to be inspected, the other embodiments are favorable.

The present invention is not limited to the method and the arrangement of the embodiments described above and various changes and modifications may be made without departing from the scope of the present invention. The present invention is applicable to an ultrasonic wave propagating method and an ultrasonic propagating device and an ultrasonic testing device using the method for propagation of a plate wave Ws between the probe (a transmitter or a receiver) and the test piece 100 through not only the air but also any gas.

INDUSTRIAL APPLICABILITY

The ultrasonic wave testing method and apparatus according to the present invention are favorable for use in the inspection of composite or lengthened materials such as aerospace components or propellers of an air craft for flaws or defects at stability and quickness.

What is claimed is:

1. An ultrasonic testing method for transmitting an ultrasonic wave from a transmitter to generate a plate wave in a test piece and receiving at a receiver the plate wave passed through a test piece to inspect the test piece along a propagation path of the plate wave, comprising the steps of:
    providing a probe, which acts as either another transmitter or another receiver, between the transmitter and the receiver which are arranged for transmitting or receiving the ultrasonic wave or the plate wave across a gaseous substance;
    mounting the transmitter, the receiver, and the probe on a probe holding mechanism respectively which have support legs placed directly on a surface of the test piece, which is selected from aerospace devices, composite materials, and lengthened materials having curves, bends, or branches, and are arranged movable in relation to the test piece so that the transmitter or the receiver can remain held at a desired angle to the surface of the test piece;
    holding the support legs in direct contact with the surface of the test piece at a location off the propagation path of the plate wave extending from the transmitter to the receiver so that the probe is suspended by the support legs to bridge, with no direct contact, over the propagation path while the probe holding mechanisms are arranged to move the transmitter, the receiver, and the probe simultaneously in relation to the test piece; and
    passing the plate wave beneath the probe while directing the probe to transmit the ultrasonic wave or receive the plate wave.

2. An ultrasonic testing method for transmitting an ultrasonic wave from a transmitter to generate a plate wave in a test piece and receiving at a receiver the plate wave passed through the test piece to inspect the test piece along a propagation path of the plate wave, comprising the steps of:
    emitting the plate wave at the forward route from the transmitter and receiving a reflection of the plate wave reflected by a target region of the test piece with the receiver, the transmitter and the receiver both arranged for transmitting or receiving the ultrasonic wave or the plate wave across a gaseous substance;

mounting the transmitter and the receiver on a probe holding mechanism respectively which have support legs placed directly on a surface of the test piece, which is selected from aerospace devices, composite materials, and lengthened materials having curves, bends, or branches, and are arranged movable in relation to the test piece so that the transmitter or the receiver can remain held at a desired angle to the surface of the test piece;

holding the support legs in direct contact with the surface of the test piece at a location off the propagation path of both the forward route of the plate wave and the reflection of the plate wave so that the transmitter and the receiver are suspended by the support legs to bridge, with no direct contact, over the propagation path of both the forward route of the plate wave and the reflection of the plate wave while the probe holding mechanism is arranged for moving the transmitter and the receiver simultaneously in relation to the test piece; and passing the plate wave emitted from the transmitter, reflected by the target region of the test piece, and propagated towards the receiver beneath the transmitter or the receiver located on the way of the propagation path while transmitting the ultrasonic wave from the transmitter or receiving the reflection of the plate wave with the receiver.

3. An ultrasonic testing method according to claim 1 or 2, wherein the probe is a focusing type probe.

4. An ultrasonic testing method according to claim 1 or 2, wherein the transmitter and the receiver are moved in relation to the test piece along a direction which extends at a right angle to the propagation path of the plate wave.

5. An ultrasonic testing method according to claim 1 or 2, wherein the transmitter and the receiver are moved in relation to the test piece along a direction aligned with the propagation path of the plate wave.

6. An ultrasonic testing device for use with the ultrasonic wave propagating method defined in claim 1 or 2, wherein
   the transmitter or the receiver is held by the probe holding mechanism and
   the probe holding mechanism is mounted to a supporting frame while remains urged by a pressing member against the supporting frame so that support legs of the probe holding mechanism are placed directly on the surface of the test piece.

7. An ultrasonic testing device having a transmitter for emitting an ultrasonic wave towards a test piece to generate a plate wave in the test piece and a receiver for receiving the plate wave passed through the test piece, whereby the test piece can be inspected along a propagation path of the plate wave by the receiver receiving the plate wave, comprising:
   a probe holding mechanism for holding the transmitter and the receiver respectively which are arranged for transmitting or receiving the ultrasonic wave or the plate wave across a gaseous substance, the probe holding mechanism having support legs placed directly on a surface of the test piece, which is selected from aerospace devices, composite materials, and lengthened materials having curves, bends, or branches, and arranged movable in relation to the test piece so that the transmitter or the receiver can remain held at a desired angle to the surface of the test piece;

a supporting frame provided to which the probe holding mechanism is mounted so that the transmitter and the receiver can move simultaneously in relation to the test piece; and a pressing member provided for urging the support legs of the probe holding mechanism by pressure directly against the surface of the test piece downwardly of the supporting frame at a location off the propagation path of the plate wave so that the transmitter and the receiver are suspended by the support legs to bridge, with no direct contact, over the propagation path of the plate wave.

8. An ultrasonic testing device having a transmitter for emitting an ultrasonic wave towards a test piece to generate a plate wave in the test piece and a receiver for receiving the plate wave passed through the test piece, whereby the test piece can be inspected along a propagation path of the plate wave by the receiver receiving the plate wave, comprising:
   a probe holding mechanism for holding the transmitter and the receiver respectively which are arranged for transmitting or receiving the ultrasonic wave or the plate wave across a gaseous substance, the probe holding mechanism having support legs placed directly on a surface of the test piece, which is selected from aerospace devices, composite materials, and lengthened materials having curves, bends, or branches, and arranged movable in relation to the test piece so that the transmitter or the receiver can remain held at a desired angle to the surface of the test piece, the support legs of the probe holding mechanism being located as spaced from each other at least along the propagation path of the plate wave;

a supporting frame provided to which the probes holding mechanism is mounted so that the transmitter and the receiver can move simultaneously in relation to the test piece;

a rocking mechanism provided between the probe holding mechanism and the supporting frame for rocking the transmitter and the receiver on the axis which extends at a right angle to at least the propagation path of the plate wave in relation to the supporting frame; and a pressing member provided for urging the support legs of the probe holding mechanism by pressure directly against the surface of the test piece downwardly of the supporting frame at a location off the propagation path of the plate wave so that the transmitter and the receiver are suspended by the support legs to bridge, with no direct contact, over the propagation path of the plate wave.

9. An ultrasonic testing device according to claim 7 or 8, wherein
   the supporting legs are equipped with wheels for running thus to move the transmitter and the receiver in relation to the test piece.

10. An ultrasonic testing method according to claim 1, wherein
    the test piece is divided into a plurality of target regions to which each of a plurality of the receivers are allocated respectively.

11. An ultrasonic testing method according to claim 2, wherein
    the test piece is divided into a plurality of target regions to which each of a plurality of the receivers are allocated respectively.

* * * * *